US005560934A

United States Patent [19]

Afzali-Ardakani et al.

[11] Patent Number: 5,560,934
[45] Date of Patent: Oct. 1, 1996

[54] CLEAVABLE DIEPOXIDE FOR REMOVABLE EPOXY COMPOSITIONS

[75] Inventors: Ali Afzali-Ardakani, Yorktown Heights; Stephen L. Buchwalter, Hopewell Junction, both of N.Y.; Jeffrey D. Gelorme, Plainville, Conn.; Laura L. Kosbar, Mohegan Lake, N.Y.; Bert H. Newman, Carmel, N.Y.; Frank L. Pompeo, Walden, N.Y.

[73] Assignee: International Business Machines Corporation, Armonk, N.Y.

[21] Appl. No.: 480,403

[22] Filed: Jun. 7, 1995

Related U.S. Application Data

[60] Division of Ser. No. 210,879, Mar. 18, 1994, Pat. No. 5,512,613, which is a continuation-in-part of Ser. No. 755,253, Sep. 5, 1991, abandoned.

[51] Int. Cl.⁶ .......................... C08G 59/00; C08G 63/00
[52] U.S. Cl. .......................... 424/497; 134/38; 134/42; 427/386; 428/620; 428/626; 428/413; 428/414; 428/416; 428/417; 428/402.21; 428/901; 528/93; 528/94; 528/110; 528/297; 528/365
[58] Field of Search .................... 528/93, 94, 110, 528/297, 365; 134/38, 42; 428/620, 626, 413, 414, 416, 417, 901, 402.21; 424/497; 427/386

[56] References Cited

U.S. PATENT DOCUMENTS

| | | | |
|---|---|---|---|
| 2,895,962 | 7/1959 | Fischer | 260/340.7 |
| 2,896,462 | 7/1959 | Mottu | 74/334 |
| 3,023,174 | 2/1962 | Batzer et al. | 528/297 |
| 3,264,235 | 8/1966 | Hustinx | 260/18 |
| 3,759,954 | 9/1973 | Batzer et al. | 260/340.7 |
| 3,879,422 | 4/1975 | Batzer et al. | 260/340.7 |
| 3,928,230 | 12/1975 | Unsworth et al. | 252/316 |
| 3,956,317 | 5/1976 | Batzer et al. | 260/340.7 |
| 4,153,586 | 5/1979 | Hockswender et al. | 260/18 EP |
| 4,159,221 | 1/1979 | Schuessler et al. | 156/285 |
| 4,315,830 | 2/1982 | French et al. | 252/182 |
| 4,741,784 | 5/1988 | Roeser, Jr. | 134/38 |

FOREIGN PATENT DOCUMENTS 0297030  5/1986  European Pat. Off. .

OTHER PUBLICATIONS

Lee and Neville, "Handbook of Epoxy Resins", McGraw–Hill, 1967, pp. 12–3 and 12–12.

Griffith (ACS Symposium Series) "Epxoy Resin Chemistry 1978", 114, pp. 5–7.

Sastri and Tesoro, "J. Appl. Polymer Sci.", 1990, 39 1425–1457.

Primary Examiner—Frederick Krass
Attorney, Agent, or Firm—Thomas A. Beck

[57] ABSTRACT

A cleavable epoxy resin composition suitable for encapsulating electronic chips comprising the cured reaction product of a diepoxide containing a cyclic anhydride curing agent and an amine promoter.

29 Claims, 4 Drawing Sheets

Hydrolysis in 1/1 Water/Ethanol (no acid)

Appearance of 3-cyclohexene-1-methanol from its acetals (gas chromatography)

FIG. 5

Shear Modulus vs. Temperature
Effect of Humidity Exposure

ACETAL/75phr HHPA/DBU

CLEAVABLE DIEPOXIDE FOR REMOVABLE EPOXY COMPOSITIONS

This application is a division of application Ser. No. 08/210,879, filed Mar. 18, 1994, now U.S. Pat. No. 5,512, 613 which is a continuation-in-part of U.S. patent application Ser. No. 07/755,253 filed Sep. 5, 1991 now abandoned.

TECHNICAL FIELD OF THE INVENTION

The present invention relates to a cleavable epoxy resin composition. Epoxy compositions are widely used as coatings, adhesives, structural components, and encapsulants. As thermosetting compositions, the epoxy materials are difficult or impossible to remove after curing. The present invention overcomes this limitation by incorporating a cleavable link in the diepoxide monomer which allows the thermoset network to be broken down in special solvents. This improvement is advantageous in many applications of epoxy compositions because it allows the epoxy to be removed for repair, replacement, recovery, or recycling of the article of which the epoxy is a part. For example, in the case of encapsulation or reinforcement of solder joints in microelectronic applications, removal of the epoxy allows replacement of obsolete or defective devices, saving the cost of discarding other valuable components in a microelectronic assembly.

The solvent system used to remove the cured diepoxide is another aspect of the present invention. Certain solvent systems have been found which readily dissolve the cured cleavable diepoxide compositions without degrading other materials, for example the copper wiring or the insulating dielectric material of printed circuit cards. The solvent systems used in accordance with the present invention provide an epoxy removal process compatible with manufacturing and environmental concerns.

THE PRIOR ART

Epoxy resins are of great importance for a number of diverse applications including coatings, adhesives, structural materials, electrical insulation, encapsulants, etc. The attributes of epoxy formulations which probably best explain their wide utility is the combination of processability prior to curing—low viscosity without the need for solvents—with outstanding properties after curing—toughness, adhesion, and solvent resistance. These attributes are essentially those of a thermosetting plastic, and indeed epoxy formulations are some of the most important members of the thermosetting class of materials.

Another attribute of the epoxy thermosets is their intractability after curing. This intractability is only another aspect of the chemistry of thermosets, which makes use of a curing reaction to convert low molecular weight precursors to a network polymer of essentially infinite molecular weight. The intractability of thermosets, however, is becoming more of a liability because of concerns about their longevity in the environment. Also, many manufacturers are taking responsibility for disposal or recycling of their products, or they are being required to do so by government regulation. As part of this trend, the concept of design for disassembly is one that is gaining in favor. Intractable thermosets are not compatible with this concept, whether they are used as structural components, adhesives, or encapsulants. If, however, the thermoset itself is designed for disassembly on the molecular scale, it is possible that the many advantages of thermosets can be retained without the disadvantage of intractability. As demand increases for recyclable products, cleavable diepoxide materials may well offer a means of maintaining the utility of thermoset materials.

Griffith (ACS Symposium Series: Epoxy Resin Chemistry, 1978, 114, pp 5–7; and Org. Coat. Plast. 1978, 39, pp. 209–211) has discussed the concept of "command-destruct" epoxy compositions and synthesized two examples. One was a diglycidyl ether containing olefinic unsaturation, which after curing with appropriate crosslinking agents could be degraded by oxidation of the olefinic unsaturation with a strong oxidizing agent such as permanganate. The second example contained carbamate linkages which could be cleaved by strong acids. The chemistry of these two examples is quite different from that disclosed in the present invention, and the harsh chemicals needed for degradation of the cured networks in the two cases disclosed by Griffith would limit their utility.

Sastri and Tesoro (J. Appl. Polym. Sci., 1990, 39 1425–1457) have published experiments on reversible crosslinking of epoxy resins using a disulfide link. The structure of these materials is also quite different from that of materials of the present invention. Also, dissolution of the epoxies cited in the article requires pulverization of the epoxy to a powder and many hours exposure to oxidizing agents. This dissolution process is also quite different from that disclosed herein, as it uses different chemicals and it would require destruction of the devices in order to pulverize the epoxy.

U.S. Pat. No. 3,023,174 to Batzer et al. discloses compositions based on diepoxides having linear ketal or acetal linkages. There is no mention of the possible utility of such diepoxides with respect to cleavability in dilute acid as disclosed in the present invention. In fact, stability of the cured ketal diepoxide in strong acid is claimed in Example 16 of Batzer et al. Accordingly, this patent does not render the present invention obvious. Batzer et al. do not disclose any solvent or mixture of solvents capable of dissolving the cured epoxy compositions. This reference does not recognize and thus does not distinguish the properties of compositions based on diepoxides with linear acetal or ketal links from any other diepoxides, and thus it in no way anticipates nor does it render obvious that certain compositions based on the specific diepoxides of Batzer et al. are readily degraded by ambient humidity; nor does it disclose or render obvious the particular compositions of the present invention which are stable to ambient humidity. Control over the stability of the cured compositions to ambient moisture is essential for applications of epoxy compositions. Control over the stability of the compositions cannot be predicted from Batzer et al. since no enabling teaching concerning stability or instability is disclosed.

U.S. Pat. No. 4,159,221 discloses a method for sealing an electronic circuit package. The reference discloses that the sealant used is an epoxy which is asserted to be readily soluble after being cured. The epoxy described in the reference is a conventional commercial bis-phenol A diglycidyl ether crosslinked with diaminodiphenylsulfone. The amount of the crosslinking agent is quite low. According to Lee and Neville (H. Lee and K. Neville, Handbook of Epoxy Resins, McGraw-Hill, 1967, pp. 8—8, 8–9), stoichiometric amounts of diaminodiphenylsulfone cross linking agent with bis-phenol A diglycidyl ether (DGEBA) would be 33 parts/100 parts DGEBA. The amount used in the reference is only 10 parts/100. It has been determined that curing with aromatic diamines such as diaminodiphenylsulfone is very sluggish, so without any stipulation given as to cure temperature given in the reference what little crosslinking agent was used was not completely reacted. It is well known that a properly cured conventional epoxy will not be soluble. A partially cured epoxy, such as is disclosed in the reference, may be soluble and may serve some function in their application but it will not possess the physical properties needed for most applications of epoxy compositions nor is it comparable in performance to the compositions of the present invention.

U.S. Pat. No. 2,896,462 discloses diepoxides containing cyclic acetal groups. The introduction portion of this reference discusses the expectation that acetals will be sensitive to degradation by acids and claims that the cyclic acetals in fact are surprisingly resistant to acids. There is no mention of the utility of an epoxide that is cleavable in acid nor is such an acid disclosed.

U.S. Pat. Nos. 3,759,954; 3,879,422 and 3,956,317 all disclose compositions of matter covering diepoxides containing one or more cyclic acetals and ketals. Although these patents disclose ketal and acetal diepoxides, there is no mention of cleavability of the epoxides nor of their utility in epoxy compositions that are removable after curing.

Experimental tests have confirmed that diepoxides linked by cyclic acetals are not cleavable, i.e. cured compositions based on them are not removable. For example, under conditions similar to those used to cleave the compositions of the present invention after curing, a commercial epoxide cured the same way and containing a cyclic acetal group is unaffected. Even hydrochloric acid does not degrade the epoxides containing the cyclic acetal group. Accordingly, the diepoxides containing cyclic acetals disclosed in these patents are not suitable for the purposes set forth herein and do not render the invention obvious.

U.S. Pat. No. 3,264,235 discloses soluble reaction products of aromatic epoxides and silicates. These compounds are not pertinent relative to the present invention.

Epoxy encapsulants are commonly used in microelectronic packaging because of their processability as low viscosity thermosetting materials and because of their outstanding mechanical properties after thermal curing. They are particularly valuable for reinforcement of solder joints against thermal fatigue. A severe limitation of the epoxy reinforcement for the solder joints is the fact that cured epoxy resins are insoluble and infusible, which means that the reinforced solder joints cannot be reworked. Because the inability to replace one defective component on a microelectronic assembly renders all the other valuable components on that assembly useless, the non-reworkability of conventional epoxy materials is a severe limitation on their applicability for solder reinforcement.

Thus, the cleavable diepoxide compositions of the present invention are of particular utility for microelectronic applications. For these applications, stability to ambient moisture is essential because degradation in their ability to reinforce the solder joints cannot be tolerated.

In other applications, slow degradation of the epoxy in the environment may be a desirable property, such as for controlled release of pharmaceuticals, pesticides, fertilizers or for biodegradable consumer packaging.

For the compositions of the present invention, the prior art discussed above does not anticipate the ability to remove them in certain solvents, nor the ability to modify the compositions to be degradable at a controlled rate by ambient moisture, nor the ability to stabilize them against degradation by moisture.

SUMMARY OF THE INVENTION

Cycloaliphatic epoxides are a class of epoxy resins particularly useful for a variety of applications including electrical insulation, potting, encapsulation, coatings, etc. They are generally formulated with a cyclic anhydride curing agent such as hexahydrophthalic anhydride (HHPA), which reacts with the epoxy in the presence of an amine catalyst to form a thermoset network during thermal curing. Because this network extends to macro-scale dimensions, it is insoluble and infusible, i.e. intractable.

The present invention is based on the recognition that the intractability of the cured epoxy network results from the tetrafunctional nature of the diepoxide starting material in its reaction with the difunctional cyclic anhydride. If the epoxide was only difunctional as would be the case with a monoepoxide, reaction with the difunctional anhydride could only form a linear polymer not a highly crosslinked network polymer. Thus, the link between the two epoxy groups of the diepoxide is responsible for the network formation; and cleavage of such links would convert the network immediately to a collection of small molecules, which would be soluble.

In searching for appropriate structures that can serve as links for the diepoxide, the following criteria are important.

1. The link should be sufficiently stable to permit the network to perform its function in a specific application;
2. The link should be readily cleaved under specific conditions;
3. The link should be unreactive in the curing reaction of the epoxy network;
4. A practical synthesis of the diepoxide containing the link should be available.

Figure 1:
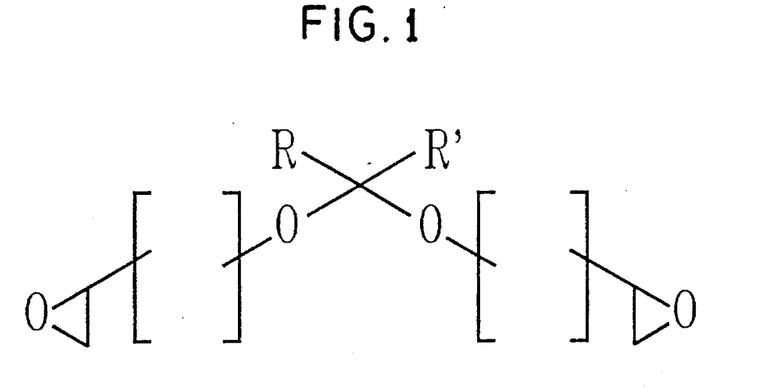
FIG. 1 is the generalized structure of diepoxides containing linear acetal links.
Figure 2:
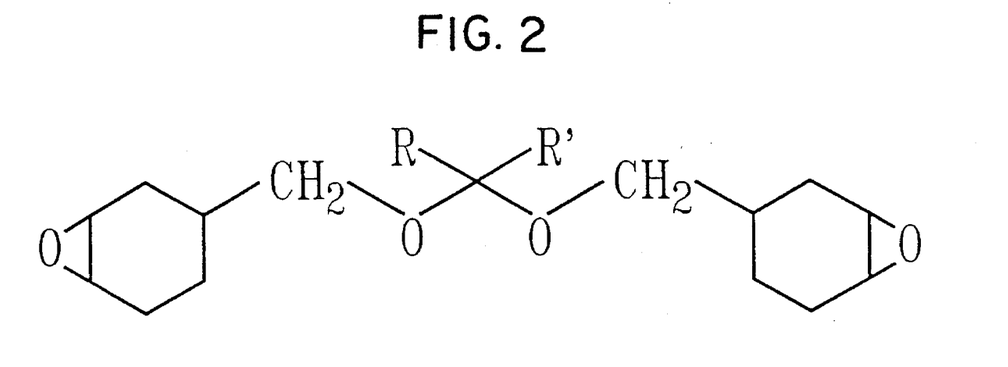
FIG. 2 is the preferred structure of diepoxides containing linear acetal links.
Figure 3:
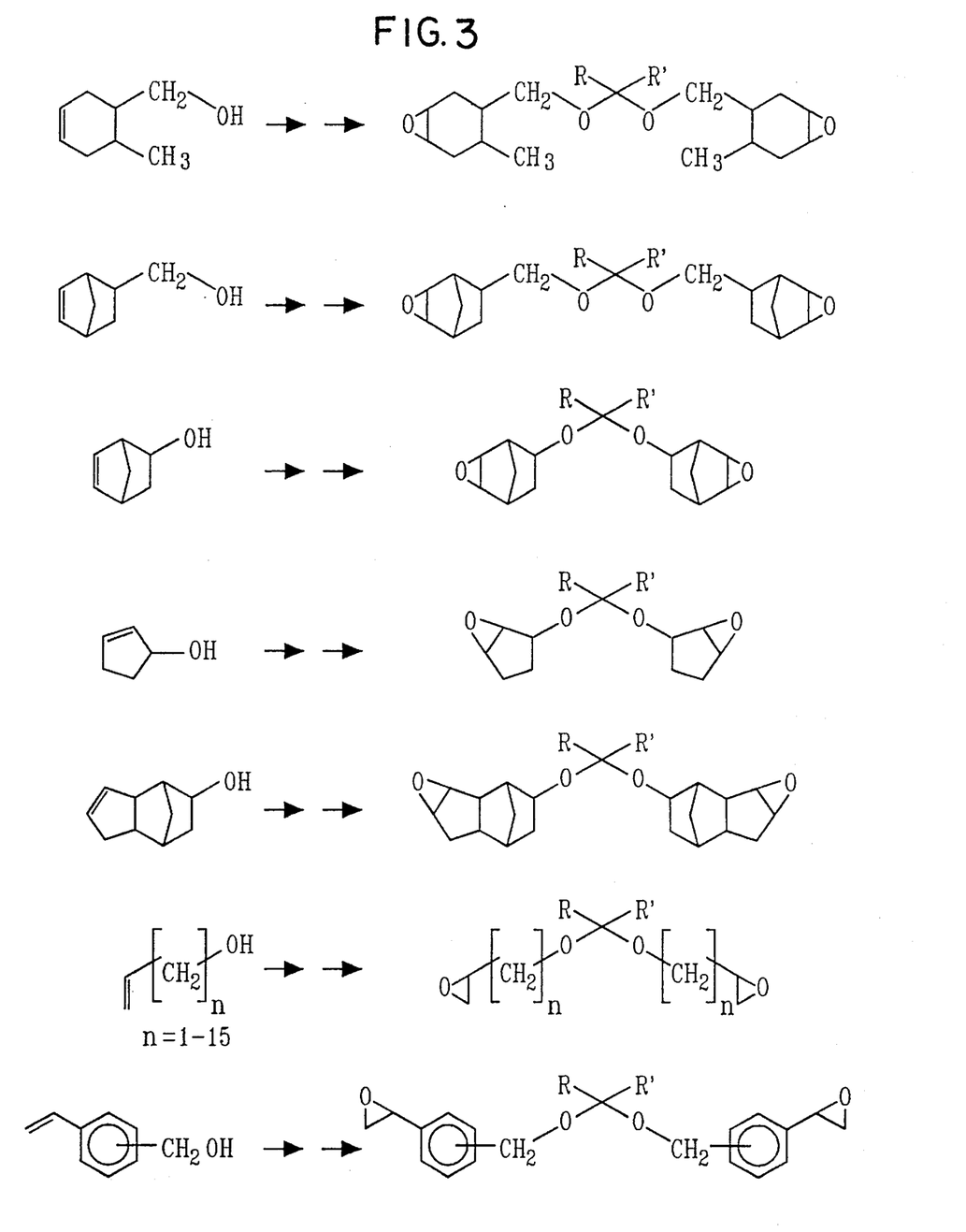
FIG. 3 depicts examples of various epoxides that can be used in accordance with the present invention.

The acetal group has been identified as a structure meeting the above criteria. For the purposes of this invention, the term "acetal" refers to the 1,1-dialkoxy group as depicted in FIGS. 1–3 where R and R' can be alkyl, aryl, aralkyl or hydrogen. The general use of the term "acetal" includes ketals (with R and R'=alkyl, aryl, or aralkyl), acetals (with R=alkyl, aryl or aralkyl and R'=H) and formals (R and R'=H). As disclosed in Advanced Organic Chemistry, J. March, 3rd Edition, Wiley Interscience (1985), pp. 329–331, the known organic chemistry of acetals indicates that they are stable to hydrolysis in the absence of acids, but break down readily in acid, even weak acids. Acetals are not subject to reactions similar to those of epoxy groups, and thus an acetal link should not be affected by the curing reaction of the epoxy.

Acetals can be hydrolyzed in acidic aqueous solutions, but they are also susceptible to trans-etherification under acidic conditions. Because the network fragments are organic solvent-soluble and not water-soluble, it has been found that the best solvents for dissolution of the cleavable networks are those containing an alcohol and some organic acid such as methanesulfonic acid or p-toluenesulfonic acid.

Figure 4:
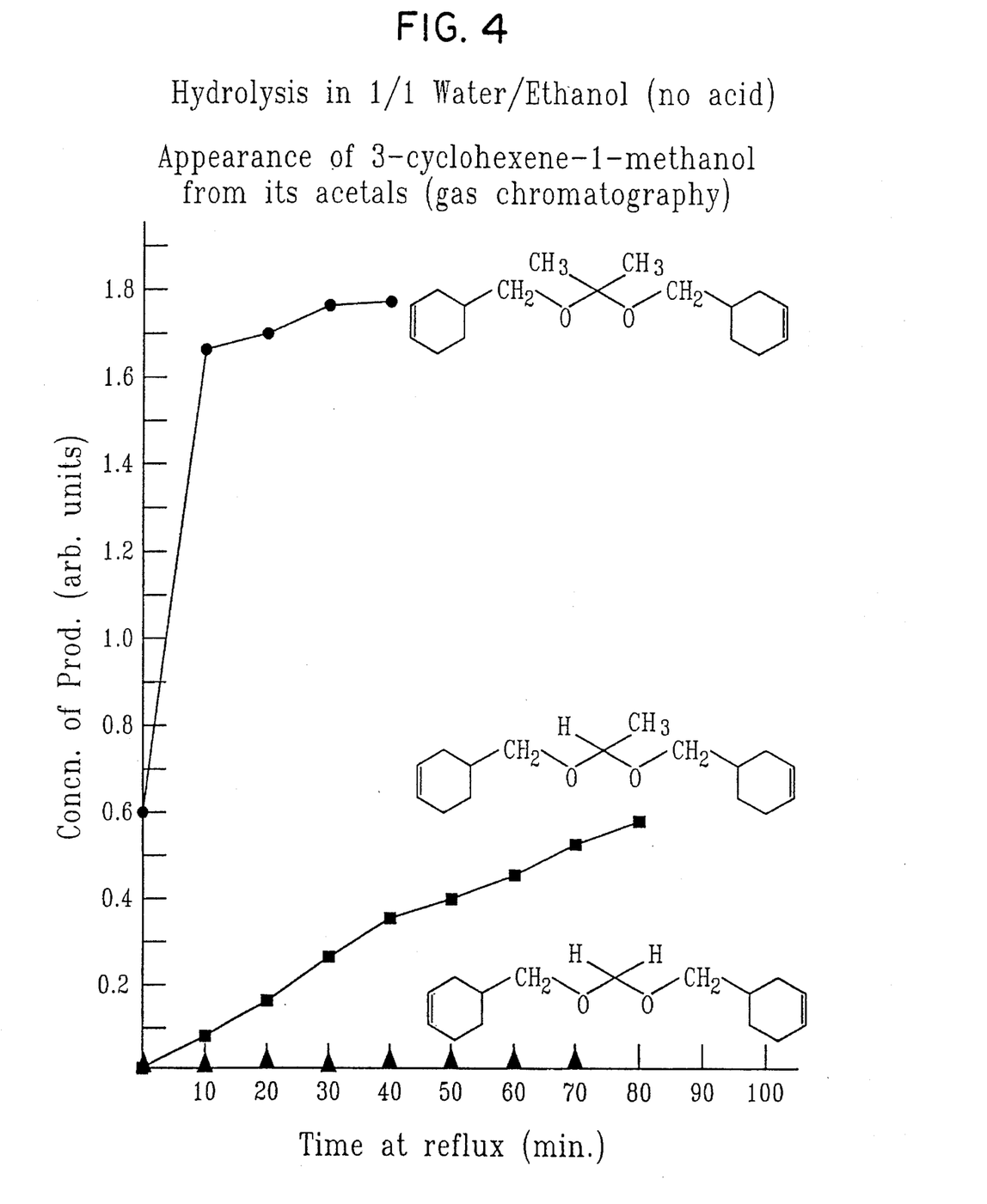
FIG. 4 depicts the relative rate of hydrolysis of ketal, acetal and formal links (see Example 12).

Control of the degradability/stability of the compositions with respect to ambient moisture is achieved, pursuant to the present invention, by using two variables in the formulation. First, the structure of the cleavable link can be varied to adjust the stability of the link to hydrolysis. As is well known (see March, as cited above), the rate of hydrolysis of acetals is affected by the substituents on the central carbon of the acetal. Considering for illustration purposes only methyl and hydrogen substituents, the formal, with two hydrogens on the central carbon is slowest to hydrolyze; the acetal, with one hydrogen and one methyl, hydrolyzes considerably more easily; and the ketal, with two methyls, hydrolyzes the fastest of the three. FIG. 4 shows actual data on hydrolysis in boiling water of a formal, acetal and ketal with structures shown in the Figure. By choosing diepoxides linked by formal, acetal, and ketal groups, or by choosing some mixture of these; the formulator can adjust the degradability of the resulting thermoset network to match the requirements of his application. For some applications, addition of conventional, non-cleavable diepoxides such as 3,4-epoxycyclohexylmethyl 3,4-epoxycyclohexanecarboxylate or bisphenol A diglycidyl ether, may be advantageous.

The other variable in the formulation controlling stability is the ratio of cyclic anhydride to epoxy. It has been discovered that if this ratio, on an equivalence basis, is kept below 0.90, the stability against moisture is markedly enhanced. The reason is that any unreacted anhydride after the curing reaction is complete will readily hydrolyze in the presence of moisture to generate carboxylic acid. This acid in the network will catalyze the cleavage of the acetal links, leading to relatively rapid degradation of the network by moisture. By using an excess of the diepoxide, all traces of anhydride are reacted, leaving none to generate acid and catalyze the degradation.

Lowering the anhydride level in the cycloaliphatic epoxide formulation means that the mixture is out of stoichiometric balance, with excess epoxy groups. Without any further changes, the network will be lower in crosslink density and hence considerably lower in glass transition temperature (Tg). For applications which require both high moisture stability and a high Tg, such as for example, microelectronic encapsulation or solder joint reinforcement, a means of raising the Tg of formulations containing an anhydride/epoxy ratio of less than 0.90 is needed.

Figure 5:
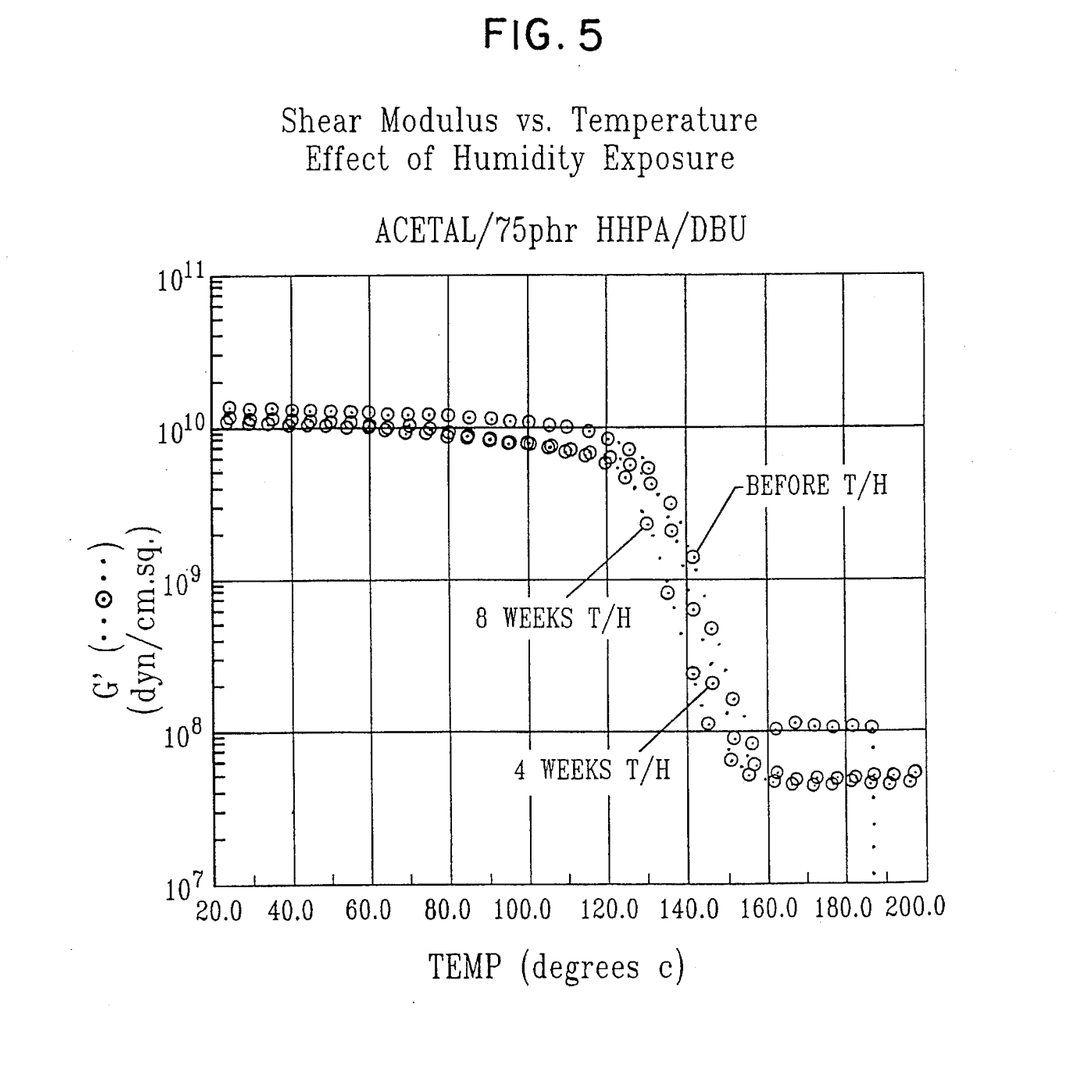
FIG. 5 exemplifies the mechanical properties and humidity stability thereof that can be achieved pursuant to the present invention (see Examples 10 and 11).

Part of the present invention is the discovery that certain 1,3-diazao compounds promote epoxy-epoxy reactions, thereby increasing the crosslink density and Tg of formulations with anhydride/epoxy ratios of less than 0.90. Thus, for those applications requiring both high moisture stability and high Tg, these compounds can be used. Shear modulus vs. temperature measurements shown in FIG. 5 illustrate the high Tg and moisture stability achievable using one of the 1,3-diaza compounds an anhydride/epoxy ratio of about 0.71.

The compounds effective as catalysts in raising the Tg of formulations containing anhydride/epoxy ratios less than 0.9 are those 1,3-diaza compounds in which one nitrogen is doubly bonded to the carbon connecting the two nitrogens and in which the second nitrogen is a tertiary amine, i.e. it has no active hydrogens. Stated alternatively, the 1,3-diaza compound has two nitrogen atoms with one nitrogen atom doubly bonded to a central carbon and singly bonded to two other carbon atoms, with the other nitrogen atom singly bonded to the central carbon and singly bonded to two other carbon atoms. The 1,3-diaza structure can be part of a cyclic or a bicyclic structure. Examples include 1-methylimidazole, propoxylated imidazole, 1-benzylimidazole, 1,8-diazabicyclo[5.4.0]undec-7-ene, and 1,5-diazabicyclo[4.3.0]non-5-ene. Conventional imidazole catalysts well known in the art such as 2-ethyl-4-methylimidazole, which contain an active hydrogen on one nitrogen, are not effective as catalysts for epoxy-epoxy reactions in these formulations.

The invention described herein is the family of epoxy compositions which are removable in certain solvents because of the cleavable acetal link connecting the epoxy groups. The utility of these compositions depends on previously unknown formulation adjustments, as described above, to achieve the environmental stability needed for the specific application.

DETAILED DESCRIPTION OF THE PREFERRED EMBODIMENT OF THE INVENTION

Any of the specific diepoxides of the present invention as depicted in FIGS. 2 and 3 are synthesized and then mixed with a cyclic anhydride, a hydroxy functional initiator, an amine promoter, and, optionally, a flexibilizer and an inorganic filler such as silica.

The preferred diepoxide structure is acetaldehyde bis-(3, 4-epoxycyclohexylmethyl) acetal (more conveniently known as acetal diepoxide).

The epoxy structures suitable for use in this invention are those derived from olefinic alcohols. The alcohol functionality preferably is an aliphatic primary or secondary alcohol group, and the olefinic functionality must be suitable for reaction with an epoxidation reagent known in the art, such as peracetic acid, perbenzoic acid, meta-chloroperbenzoic acid, potassium peroxymonosulfate, and the like.

The cyclic anhydride can be any of the well known anhydride curing agents (see, for example, Lee and Neville, Handbook of Epoxy Resins, McGraw-Hill, 1967, Chapter 12) including hexahydrophthalic anhydride, methyl-hexahydrophthalic anhydride, nadic methyl anhydride, maleic anhydride, and the like. For microelectronic applications, the preferred compositions will have anhydride/epoxy equivalence ratios of 0.90 or less to minimize degradation by moisture.

The hydroxy functional initiator can be any high boiling alcohol or polyol, such as ethylene glycol, diethylene glycol or the like. Optionally the flexibilizer can serve as the hydroxy functional initiator, by using a polyether diol such as polyethylene glycol, polypropylene glycol, poly(caprolactone)diol or poly(oxybutylene)diol.

The amine promoter can be any of the tertiary-amines known in the art such as benzyldimethyl amine, triethyl amine, pyridine and the like. For microelectronic applications, the preferred amine promoters are those which will raise the Tg of the moisture-stable formulations, for example, 1,5-diazabicyclo [4.3.0]non-5-ene, 1,8-diazabicyclo[5.4.0]undec-7-ene, 1-methylimidazole, or propoxylated imidazole.

The optional inorganic filler can be any of the powdered solids known in the art, such as alumina, silica, zinc oxide, etc. For microelectronic applications, the preferred filler is silica. Encapsulants are commonly filled with an inorganic powder to reduce the coefficient of thermal expansion. Suitable filler materials include alumina, silica, and the like. The preferred filler is a highly purified form of silica with particle size of 25 microns or less. The amount of filler may vary but is preferred in the range 40–70% on a weight basis.

The optional flexibilizer can be any of the well known materials used for this purpose such as the Union Carbide ERL-4350, LHT-240 or the B. F. Goodrich butadiene-acrylonitrile copolymers sold under the trade name HYCAR. In addition, any polyetherdiol or polyesterdiol can be used as a flexibilizer including polyethlene glycol, polypropylene glycol, poly(caprolactone)diol, or poly(oxybutylene)diol. A preferred flexibilizer is one which does not significantly depress the glass transition temperature of the formulation, such as the maleic anhydride adducts of polybutadiene resins sold by Ricon Resins as R-130.

Pursuant to the present invention, the combination of the low viscosity of the epoxy precursor mixture and the high modulus and relatively low CTE of the cured matrix has been found to be advantageous for an important device protection application. A particularly useful embodiment is the protection of solder ball interconnections of chips to ceramic or other substrates. A low viscosity precursor mixture can efficiently and completely fill the spaces between chip and substrate and envelop all interconnections with epoxy. Cured epoxy generally provides remarkable enhancement of the solder ball interconnections with respect to times to failure in thermal cycling. Because of the ability, in view of this reinforcement, to mount large chips that would otherwise show unacceptable failure rates, this application for epoxy materials generates substantial interest. Wide application of this reinforcement, however, would require that the epoxy be removable in order to allow rework of a single chip in a microelectronic assembly. As stated above, cured epoxy resins are known for their intractability. Use of the compositions based on the cleavable diepoxides provides equivalent performance with added benefit of removability.

The epoxy formulations are cured by heating at 90°–200° C. for about 1–6 hours to form a hard tack-free solid. The preferred curing schedule includes a gel cure for about one hour at 80°–100° C., followed by a post-cure of about 2 hours at 135°–165° C.

After curing, the cleavable diepoxide formulations can be dissolved by hydrolysis or transetherification of the cleavable link, which is an acetal group connecting two cycloaliphatic epoxy groups. Acetals are generally easily cleaved in aqueous acid, but in order to dissolve the matrix, an organic solvent is also needed. For the purposes of this invention, suitable acids include organic acids such as acetic acid, propionic acid, chloroacetic acid, benzoic acid and the like; sulfonic acids such as benzenesulfonic acid, p-toluenesulfonic acid, methanesulfonic acid and the like; inorganic acids such as sulfuric acid, phosphoric acid, hydrochloric acid, and the like; and Lewis acids such as boron trifluoride etherate, aluminum chloride, stannic chloride and the like. The solvent mixtures are given only as examples to illustrate the type of solvents and acids to be used. The preferred acids are methanesulfonic acid and p-toluenesulfonic acid.

The temperature of the solvent mixture can be 25° C. or above, but for most rapid dissolution the solvents should be heated to boiling or near boiling. One useful mixture is that of ethanol, acetic acid, and water which is particularly effective in dissolving the cured formulations based on the ketal diepoxide. Other suitable solvent mixtures include a combination of gamma-butyrolactone, water, and phosphoric acid and a combination of butanol, acetic acid and water. Acetals are also susceptible to trans-etherification under acidic conditions. It thus is possible to use an alcohol as both the solvent and the reactant, removing the necessity of adding water to the system thereby reducing the likelihood of corrosion of any metallic components of the device. For example, a mixture of ethanol and an organic acid such as benzenesulfonic acid, para-toluenesulfonic acid, or methanesulfonic acid can be used to dissolve the cured epoxy based on the acetal diepoxide. It has been found that transetherification using a primary alcohol such as ethanol and an organic acid such as methanesulfonic acid was faster than hydrolysis in aqueous acid. An even faster dissolution rate was found by the incorporation of a portion of a less polar organic solvent such as xylene or benzyl alcohol or by the use of trifluoroethanol instead of ethanol.

The solvent used in accordance with the present invention comprises 100–10 parts, preferably about 75 parts, of a primary alcohol as exemplified by: ethanol, methanol and n-propanol; 0–90 parts, preferably about 25 parts, of a less polar organic solvent as exemplified by: benzyl alcohol, xylene, toluene; and 1–10 parts, preferably about 3 parts of an organic acid as exemplified by: methanesulfonic acid, p-toluenesulfonic acid and triflouromethanesulfonic acid. Optionally the solvent includes a surfactant and/or a corrosion inhibitor.

EXAMPLE 1

This example discloses the preparation of acetone bis-(cyclohex-3-enylmethyl) ketal: 3-cyclohexene-1-methanol (224.3 grams, 2.00 moles) was dissolved in a mixture of 2,2-dimethoxypropane (104.2 g, 1.00 m), cylohexane (330 ml), and p-toluenesulfonic acid (0.1 g). The mixture was heated to reflux through a distillation column, and the cylohexane/methanol azeo- trope (b.p. 54.2° C.) was removed over 5 hours. The head temperature gradually increased to 81° C. The yellow pot residue was cooled, and the acid was neutralized with sodium methoxide. The remaining solvent was removed on the rotary evaporator, the residue was distilled under vacuum (b.p. 99°–100°/0.8 mm Hg) to give a 74% yield of the pure diolefinic ketal identified by IR and NMR.

EXAMPLE 2

This example discloses the preparation of acetone bis-(3, 4-epoxycyclohexylmethyl) ketal (ketal diepoxide). Successful epoxidation of the diolefinic ketal required a procedure which did not include exposure of the ketal to acidic conditions. Such a procedure was found in the literature (Curci, R.; Fiorentino, M.; Troisi, L. J. Org. Chem., 1980, 45, 4758–4760) and adapted as follows. The diolefinic ketal (13.48 g, 0.051 m) was dissolved in dichloromethane (150 ml) and acetone (150 ml) and mixed with a pH 7.5/0.1M phosphate buffer (100 ml) and 18-crown-6 (1.5 g) as a phase transfer agent. The mixture was stirred in an ice bath to reduce its temperature to 6° C. before the start of the simultaneous addition of a solution of potassium peroxymonosulfate (OXONE, DuPont, 73.8 g in 400 ml deionized water containing 0.09 g of ethylenediaminetetraacetic acid) and a 0.5M KOH solution. Rapid stirring and chilling with ice were continued throughout the addition, and the relative rate of the addition of the two solutions was adjusted to keep the pH of the reaction mixture in the range 7.3–7.9. Addition of the OXONE solution was complete in 2 hours. During an additional 3.5 hours of stirring, the temperature was kept at 6°–8° C., and the pH was maintained in the above range by continued slow addition of 1. OM KOH. At the end of this time, additional dichloromethane (100 ml) was stirred in for 5 minutes. The dichloromethane phase was isolated, and the aqueous phase was shaken with additional dichloromethane (100 ml). The combined dichloromethane solutions were then dried over magnesium sulfate, filtered and evaporated to give a 95% yield of liquid diepoxide identified by IR and NMR. Epoxide equivalent weight (weight per epoxide) was 161 (theory 148).

EXAMPLE 3

This example discloses the preparation of acetaldehyde bis-(cyclohex-3-enylmethyl) acetal. The Ciba procedure as disclosed in U.S. Pat. No. 3,023,174 was followed to prepare the aforementioned composition. A mixture of 3-cyclohexene-1-methanol (75 g, 0.67M), mercuric oxide (0.5 g) and boron trifluoride diethyl etherate (0.5 g) was warmed to 55° C. before vinyl acetate (30 g, 0.35M) was added dropwise with stirring. After the addition (about 2 hours), the solution was held at 60° C. for 16 hours then left at ambient temperature for 2 days. After quenching with 28 g sodium carbonate and 125 g ice-cold water, the organic phase was combined with a 50 ml toluene extract of the aqueous phase, dried over sodium sulfate, and filtered. The solvent was removed by rotary evaporation, and the residue was distilled under vacuum at 0.4–0.5 mm. The forerun boiling at <100° C. was 0 discarded. The resultant material (36 g or 43%) was collected at 110°–125° C. and identified by IR and NMR.

EXAMPLE 4

This example discloses the preparation of acetaldehyde bis-(3,4-epoxycyclohexylmethyl) acetal (acetal diepoxide). Following the same procedure as for the ketal diepoxide disclosed in Example 2 above, a quantitive yield of acetal diepoxide was obtained, which was free of olefin by IR and NMR and had an epoxy equivalent weight of 146 (theory 141).

EXAMPLE 5

This example discloses the preparation of formaldehyde bis-(cyclohex-3-enylmethyl) acetal. The Ciba procedure was followed except that water was removed in a Dean-Stark trap to drive the reaction to completion. Spectra (IR and NMR) confirmed the structure.

EXAMPLE 6

This example discloses the preparation of formaldehyde bis-(3,4-epoxycyclohexylmethyl) acetal (formal diepoxide). Using the above-described epoxidation procedure, a material was obtained which had appreciable unreacted olefin as evidenced by IR. This was subjected to a repeat epoxidation, resulting in a 61% yield of olefin-free product (IR and NMR). Epoxy equivalent weight was 137 (theory 134).

EXAMPLE 7

This example provides curing studies. The Union Carbide cycloaliphatic diepoxide ERL-4221 (2.00 g, measured epoxy equivalent weight 141) was mixed with melted hexahydrophthalic anhydride (2.00 g), ethylene glycol (0.02 g) and propoxylated imidazole (Archem AP-5, 0.04 g). The first three components were thoroughly blended before mixing in the imidazole. The mixture was then spotted from a pipet onto microscope slides and cured at 150° for 2 hours. The spots were hard tack-free solids, as expected for a fully cured epoxy resin. Similar results were obtained with various levels of benzyldimethylamine (BDMA) instead of propoxylated imidazole. A DSC run using BDMA showed a single exotherm with maximum at 146° C.

Similarly, ketal diepoxide (2.16 g) was mixed with hexahydrophthalic anhydride (2.00 g), ethylene glycol (0.02. g) and propoxylated imidazole or benzyldimethylamine (0.04 g). After curing under the same conditions, the result was hard and tack-free as above. A DSC run had a similar exotherm to that of the commercial diepoxide (maximum 141° C.).

The acetal diepoxide (1.05 g) was also mixed with the anhydride (1.05 g), ethylene glycol (0.01 g), and BDMA (0.13 g). Its curing behavior was quite similar, hard and tack-free with an exotherm in DSC peaking at 148° C.

The formal diepoxide (0.52 g) was also mixed with the anhydride (0.507 g), ethylene glycol (0.01 g), and BDMA (0.015 g) and cured as above. No significant differences were seen in hardness or DSC (exotherm maximum 148° C.).

EXAMPLE 8

Samples of acetal diepoxide were cured with varying levels of anhydride to investigate the effect of anhydride on stability to humidity.

Example 8A

Acetal diepoxide, 100 parts by weight, was mixed with 100 parts of pre-melted hexahydrophthalic anhydride (HHPA, anhydride/epoxy equivalent ratio=0.95) and with 2.5 parts of ethylene glycol. Benzyldimethylamine, 2.5 parts, was then added and thoroughly mixed in. The clear, homogenous mixture was then spotted on microscope slides to form 10-mm diameter disks and loaded into a silicone bar mold containing five 40×10×1.5 mm cavities. The bar samples were degassed for 5 min under moderate vacuum, then all samples were cured in a convection oven at 100° C. for 1 hour and 150° C. for 2 hours.

Example 8B

A sample was prepared by exactly the same procedure as in 8A except that 90 parts of HHPA (anhydride/epoxy=0.85) was used.

Example 8C

A sample was prepared by exactly the same procedure as in 8A except that 80 parts of HHPA (anhydride/epoxy=0.76) was used.

Example 8D

A sample was prepared by exactly the same procedure as in 8A except that 70 parts of HHPA (anhydride/epoxy=0.66) was used.

Example 8E

A sample was prepared by exactly the same procedure as in 8A except that 50 parts of HHPA (anhydride/epoxy=0.47) was used.

Comparative Example 8F

The commercial cycloaliphatic epoxide, 3,4-epoxycyclohexylmethyl 3,4-epoxycyclohexanecarboxylate (Union Carbide ERL-4221), was used to prepare similar samples for comparison purposes. The composition was 100 parts ERL-4221, 100 parts HHPA (anhydride/epoxy=0.92), 2.5 parts ethylene glycol, and 2.5 parts benzyldimethylamine.

EXAMPLE 9

The moisture stability of cured epoxy samples was investigated by placing the samples into a constant temperature/humidity chamber at 85° C. and 81% relative humidity (T/H) for various times. After T/H exposure, the samples were monitored for evidence of degradation using either thermomechanical analysis or measurements of shear modulus vs. temperature.

Example 9A

Cured samples of the ketal diepoxide from Example 7 were subjected to T/H. Prior to T/H, the sample was hard with a glass transition temperature (Tg) of about 95° C. After 2–3 weeks, the sample was degraded to the point that thermomechanical analysis could not be run. Acetal diepoxide cured as in Example 7 gave variable results depending on the ratio of anhydride to epoxy.

Example 9B

The acetal samples of Examples 8A–8E were subjected to T/H. Comparison of mechanical properties was then made to the unexposed samples by measuring shear modulus vs. temperature for both exposed and unexposed samples. After one week T/H, Sample 8A showed a marked drop in Tg from 120° C. to about 40° C., and an order of magnitude decrease in modulus above the Tg. Both observations are consistent with the change in properties expected if the acetal links have been partially broken by hydrolysis in T/H.

Sample 8B also showed evidence of the same degradation after one week, but to a considerably lesser extent. The Tg decreased by 30° C., and the change in modulus was also less.

Sample 8C in contrast showed no change in mechanical properties after up to 8 weeks T/H, showing that at this anhydride/epoxy ratio the acetal links are not hydrolyzed by moisture.

Sample 8D showed essentially no change after 1 week T/H.

Sample 8E had a Tg before T/H of only 25° C. and actually showed an increase in Tg of 15° C. after 1 week T/H and moderate further increases upon longer term exposure.

Comparative Sample 8F showed essentially no change in properties after up to 8 weeks T/H, except for a reversible plasticization by absorbed water, resulting in a temporary 10° C. drop in Tg.

EXAMPLE 10

Formulations based on acetal diepoxide with anhydride/epoxy ratios less than 0.95 have low Tg's using benzyldimethylamine as catalyst. The increase in Tg observed for Sample 8E after exposure to T/H suggested that epoxy-epoxy reactions could be used to raise the Tg. To find catalysts which would increase the rate of epoxy-epoxy reaction, test formulations similar to that of Example 8C were prepared using a variety of catalysts. The curing exotherm for each formulation was measured by differential scanning calorimetry, as shown in Table I. A larger exotherm was expected with catalysts which promote the epoxy-epoxy polyetherification reaction in addition to the normal epoxy-anhydride polyesterification reaction.

The data of Table I show two categories of catalyst—those giving curing exotherms of above 200 J/g and those giving exotherms of about 150 J/g or less. Larger samples of formulations containing two catalysts in the higher exotherm category were then prepared as described in Examples 10A–D.

TABLE I

Differential Scanning Calorimetry of Acetal Diepoxide Formulations

| Amine catalyst[a, b] | Peak temperature | Exotherm (J/g)[c] |
| --- | --- | --- |
| BDMA | 149 | 147 |
| AP-5 | 140 | 303 |
| EMI | 164 | 105 |
| DBU | 141 | 221 |
| DMEA | 145 | 108 |
| DMAP | 128 | 156 |
| DBN | 146 | 292 |

[a]80 phr hexahydrophthalic anhydride, 3 phr ethylene glycol, 2.5 phr amine catalyst.
[b]BDMA: benzyldimethylamine; AP5: propoxylated imidazole (ARCHEM); EMI: 2-ethyl-4-methylimidazole; DBU: 1,8-diazabicyclo[5.4.0]undec-7-ene, DMEA: dimethylethanolamine, DMAP: 4-dimethylaminopyridine, DBN: 1,5-diazabicyclo[4.3.0]non-5-ene.
[c]5°/min scan from 30–200 C.

Example 10A

Acetal diepoxide (100 parts), HHPA (80 parts), ethylene glycol (3 parts) and propoxylated imidazole (AP5, 2.5 parts) were mixed and cured on microscope slides and in the bar molds as described in Example 8.

Example 10B

Acetal diepoxide (100 parts), HHPA (85 parts), ethylene glycol (3 parts), and 1,8-diazabicyclo[5.4.0]undec-7-ene (DBU, 2.5 parts) were mixed and cured as in Example 8.

Example 10C

Sample 10B was repeated with 80 parts of HHPA.

Example 10D

Sample 10B was repeated with 75 parts of HHPA.

EXAMPLE 11

Samples from Examples 10A–10D were subjected to T/H testing. Sample 10A showed a high Tg before T/H of about 140° C., which was decreased by about 25° C. after 1 week T/H. Samples 10B–D had Tg's before T/H of 107°, 125°, and 136° C., respectively. There was little or no change in mechanical properties observed after up to 8 weeks T/H.

EXAMPLE 12

To compare the hydrolytic stability of the ketal, acetal and formal links, the olefinic compounds as prepared in Examples 1, 3, and 5, respectively were subjected to a boiling 1/1 mixture of water and ethanol containing a small amount of benzylacetone as internal standard. Aliquots of each of the solutions were removed at various times and were analyzed by gas chromotagraphy to compare the relative rate of appearance of 3-cyclohexene- 1-methanol from each of the three olefinic compounds. The results of the analysis are depicted in FIG. 4.

EXAMPLE 13

Removal of the resins derived from the cleavable diepoxides was accomplished by exposing samples of the mixtures cured as in Example 7 to a number of solutions. Cured samples of the mixture containing the Union Carbide ERL-4221 were also exposed at the same time as a control. A solution containing a 1:1:1 volume ratio of glacial acetic acid, ethanol, and deionized water was heated to its boiling point (88° C.). The cured ketal diepoxide and the ERL-4221 control were immersed in this solution. After 6 minutes, complete dissolution of the ketal diepoxide had occurred. The control sample was unchanged. Exposure of the cured acetal diepoxide to this solvent showed much slower dissolution—after 60 minutes, the acetal was only partially dissolved. The formal diepoxide was unaffected by this solution.

Similarly, a 135:45:20 ratio of gamma-butyrolactone, water, and phosphoric acid was heated to reflux at 105°–106° C. This solvent mixture dissolved the cured ketal diepoxide in <2 minutes and the cured acetal diepoxide in 10–15 minutes. The control ER-4221 and the formal diepoxide were virtually unaffected.

EXAMPLE 14

A variety of solvent/acid systems can be used to dissolve the epoxy, and this system may be chosen to minimize attack on other materials. A system that has proven to be very benign to other materials is a solution of p-toluenesulfonic acid (PTSA) in ethanol. The ethanol acts as both the reactant and the solvent, so no water is required. Ethanol has minimal safety and waste disposal concerns, and PTSA is a solid acid that is easily handled. Acid concentrations of 0.025M to 0.5M have been found to be effective in dissolving the acetal and ketal epoxies. Samples of ketal, similar to those in Example 7, dissolved in well under 10 minutes in a refluxing solution of 0.05M PTSA, while samples of acetal dissolved in 15 minutes in 0.025M PTSA and about 4 minutes in 0.3M PTSA. These acid concentrations are low compared with concentrations of acetic acid (5.8M) or phosphoric acid (1.5M) used previously. While the PTSA/ethanol solutions caused no apparent corrosion of copper, there was a slight attack on lead-tin solder. The extent of this corrosion was significantly reduced by adding very small amounts of phosphate (as little as 0.01M)—either as a phosphate salt or phosphoric acid.

EXAMPLE 15

Another acid that can be used is methanesulfonic acid (MSA). Cured acetal diepoxide formulations as prepared in Example 7 dissolve in boiling ethanol containing 0.3M MSA in 4–5 min. The cured formal diepoxide formulations of Example 7 dissolve in this solvent in 30–60 min.

Samples from Examples 10A–10D were also subjected to boiling ethanol containing methanesulfonic acid (MSA) at 0.3M concentration. Dissolution of the epoxy disks from the microscope slides was complete in 6–40 min. A cured formulation of ERL-4221 prepared as in Example 7 was unaffected by this treatment.

Other solvent mixtures can also be used. For example, Sample 10C dissolved in a boiling mixture of ethanol and N-methylpyrrolidone (75/25) with 0.3M MSA in 19 min. Sample 10C also dissolved in a boiling mixture of ethanol and xylene (75/25) with 0.3M MSA in 8–9 min. Sample 10C dissolved in a boiling mixture of ethanol and benzyl alcohol (75/25) in 4 min. Sample 10C dissolved in a boiling 0.3M solution of MSA in 3,3,3-trifluoroethanol in 3 min.

EXAMPLE 16

A diepoxide containing a cyclic acetal link, 3,4-epoxy-hexahydrobenzaldehyde 3,4-epoxy-1,1bis(hydroxymethyl) cyclohexane acetal (Union Carbide ERL-4234) was cured in formulations similar to those of Example 7. These cured samples were subjected to 0.3M MSA in boiling ethanol for long periods. No evidence of dissolution was observed.

EXAMPLE 17

A formulation similar to that of Example 10C was prepared except 20 parts of Ricon Resins R-131 flexibilizer was added. The Tg of the cured sample was 119° C., and no change was observed after 4 weeks T/H. The sample was also soluble in solvents of Example 15.

EXAMPLE 18

A formulation similar to that of Example 10D was prepared except silica filler (fine particle size, PQ Corporation) was added to the level of 57 percent by weight. Stability in T/H and dissolution in the various solvents disclosed in Example 14 was essentially unchanged.

EXAMPLE 19

A formulation similar to that of Example 18 is prepared and charged into plastic syringes. After degassing under vacuum, the syringes are frozen at −40° C. until use. After thawing to room temperature, the epoxy is dispensed under slight pressure through a needle to the periphery of silicon chips attached by controlled collapse chip connection (C4) solder bumps to a ceramic substrate. The substrate is preheated to about 80° C. to facilitate flow of the filled epoxy to completely fill the underchip cavity and surround the C4's. After the epoxy has been applied to all devices on the substrate and flow is complete, the substrate is transferred to an oven and the epoxy is cured at 80° C. for 1 hour and then 150° C. for two hours.

As necessary for replacement of defective or obsolete chips on the substrate, the epoxy is removed by immersing the substrate in a hot mixture of ethanol, benzyl alcohol and MSA preferably excluding air. Once all the epoxy is removed, the substrate is carefully rinsed in pure ethanol, again preferably excluding air.

EXAMPLE 20

Using an epoxy formulation similar to that of Example 19, chips directly mounted on a printed circuit card by flip chip attach or by wire bonds are encapsulated in globtop fashion. After curing as previously, the printed circuit cards are ready for shipment.

For purposes of replacement of defective or obsolete components or to facilitate removal of lead-containing solder prior to disposal of the printed circuit assembly, the epoxy is easily removed as in Example 19.

EXAMPLE 21

For controlled release of agricultural chemicals such as pesticides, herbicides and fertilizers, an agrichemical mixture is mixed separately with epoxy formulations based on the formal, acetal and ketal diepoxides. Each mixture is heated in the mixing chamber to a preset viscosity, then extruded into beads, which solidify upon cooling. The beads are then post-cured at 150° C. A blend of the three varieties of beads is prepared which is varied to match the rate of release of the agrichemical desired for the target application. Slow hydrolysis of the cured epoxies in the environment gradually releases the agrichemicals, first from the beads fabricated with ketal diepoxide, next from those made with acetal diepoxide, finally from those made with formal diepoxide.

EXAMPLE 22

The agrichemical mixture of Example 21 is blended with two or more formulations of acetal diepoxide containing varying amounts of HHPA. After processing as above, beads are blended for timed release of the agrichemical based on the relative rate of hydrolysis in the environment of epoxy formulations containing varying amounts of anhydride. Over a given period of time, a constant release of agrichemical is obtained.

EXAMPLE 23

During microanalysis of various mechanical and electrical devices, a variety of electronic devices are routinely mounted in an epoxy potting compound and then subjected to cutting and polishing to expose a particular surface of the device for detailed optical and scanning electron microscopy. Recovery of the part for further analysis of other surfaces was virtually impossible with conventional epoxy potting compounds. Using the present invention technique, a formulation based on the ketal or acetal diepoxide as described in Example 7 allows removal of the potting compound as described in Examples 11–14.

EXAMPLE 24

To prepare a microporous epoxy for size exclusion chromatography or for gas separation, beads of epoxy are prepared as in Example 21 but using a blend of ERL-4221 and ketal diepoxide, along with the other components of epoxy formulations as described in Examples 7 and 8. A plurality of bead samples are prepared comprising the various samples, each of the samples is, after complete curing of the beads, exhaustively extracted with a different solvent selected from those described in Examples 11–14 to remove the ketal diepoxide portion of the blend, leaving micropores in each of the epoxy matrices. The size of the micropores is adjusted by varying the amount of ketal diepoxide in the matrix in the range 0.1–5%, the balance being ERL-4221.

In each case, the finished beads, having one characteristic pore size or having a controlled blend of pore sizes, are packed in a column through which the liquid or gaseous mixture is passed for separation by molecular size.

Having thus described our invention, what we claim as new, and desire to secure by Letters Patent is:

1. A diepoxide composition which encapsulates and protects an electronic device or assembly, said composition comprising the cured reaction product of: a diepoxide in which the connection between the two epoxy groups of the diepoxide includes a cleavable acyclic acetal group; a cyclic dicarboxylic anhydride curing agent; a 1,3-diaza compound having two nitrogen atoms with one nitrogen atom doubly bonded to a central carbon and singly bonded to one other carbon, and the other nitrogen atom singly bonded to the central carbon and singly bonded to two other carbons, said 1,3-diaza compound serving either as sole catalyst or in combination with a tertiary amine catalyst; and a hydroxy functional initiator, wherein said composition is capable of being readily cleaved and removed in acidic organic solvents.

2. The diepoxide composition of claim 1 which reinforces solder joints which are present in said electronic device or assembly.

3. The combination of claim 1 or 2 wherein said device is a silicon chip.

4. A method of coating, protecting, encapsulating, reinforcing, assembling, or fabricating a device, an article of commerce or a chemical product with a cured diepoxide composition which is capable of being readily cleaved and removed in acidic organic solvents, said epoxy composition comprising the reaction product of: a diepoxide in which the connection between the two epoxy groups of the diepoxide includes a cleavable acyclic acetal group; a cyclic dicarboxylic anhydride curing agent; a tertiary amine catalyst; and a hydroxy functional initiator.

5. The method of claim 4 in which said diepoxide is selected from the group consisting of: acetaldehyde bis-(3,4-epoxycyclohexylmethyl)acetal, acetone bis-(3,4-epoxycyclohexylmethyl)ketal, and formaldehyde bis-(3,4-epoxycyclohexylmethyl)acetal.

6. The method of claim 5, wherein said cyclic anhydride is selected from the group consisting of: hexahydrophthalic anhydride, tetrahydrophthalic anhydride, methyltetrahydrophthalic anhydride, methylhexahydrophthalic anhydride, dodecylsuccinic anhydride, nadic methyl anhydride, trimellitic anhydride, and maleic anhydride;

said catalyst is selected from the group consisting of: benzyldimethylamine, pyridine, triethylamine, choline base, stannous octoate, dimethylaminopyridine, 1,4-diazabicyclo[2.2.2]octane, 2-ethyl-4-methylimidazole, 1,8-diazabicyclo[5.4.0]undec-7-ene, 1,5-diazabicyclo[4.3.0]non-5-ene, 1-methylimidazole, 1-benzylimidazole, 1,2-dimethylimidazole, 1-benzyl-2-methylimidazole, and propoxylated imidazole; and said hydroxy-functional initiator is selected from the group consisting of: ethylene glycol, diethylene glycol, triethylene glycol, propylene glycol, diethylene glycol, triethylene glycol, propylene glycol, 1,4-cyclohexanediol, and 1,4-cyclohexanedimethanol.

7. The method of claim 6 in which said epoxy composition also contains a flexibilizer material selected from the group consisting of: butadiene-acrylonitrile rubber, polyethylene glycol, polypropylene glycol, poly(caprolactone)diol, poly(oxybutylene)diol, and poly(butadiene)/maleic anhydride adducts.

8. The method of claim 4 in which said epoxy composition is removed in a solvent at 25° C. or greater, said solvent comprising an organic solvent, an acid and water.

9. The method of claim 7 in which said epoxy composition is removed in a solvent at 25° C. or greater, said solvent comprising an organic solvent, an acid and water.

10. The method of claim 9 in which the organic solvent is ethanol and the acid is acetic acid.

11. The method of claim 9 in which the organic solvent is gamma-butyrolactone and the acid is phosphoric acid.

12. The method of claim 9 in which said solvent comprises one or more primary alcohols and an organic acid.

13. The method of claim 12 in which said primary alcohols are selected from the group consisting of methanol, ethanol, n-propanol, n-butanol, n-hexanol, benzyl alcohol, and trifluoroethanol; and the organic acid is selected from the group consisting of alkylsulfonic acids, arylsulfonic acids and aralkylsulfonic acids.

14. The method of claim 13 in which said solvent also contains a non-polar organic solvent.

15. The method of claim 13 in which the organic acid is methanesulfonic acid.

16. The method of claim 4 in which said device is an electronic device or electronic assembly.

17. A structure comprising an electronic device or assembly in which the cured composition of claim 4 encapsulates or protects said electronic device or assembly.

18. The structure of claim 17 in which said electronic device or assembly possesses at least one solder joint which is encapsulated and reinforced by said composition.

19. The structure of claim 18 in which said electronic device is a silicon integrated circuit electrically connected to a substrate with solder using controlled collapse chip connection.

20. The structure of claim 19 in which said substrate is a ceramic multichip module.

21. The structure of claim 20 in which said cured composition reinforces said solder connections.

22. The structure of claim 17 in which said assembly is a ceramic module attached to a substrate with solder balls or solder columns.

23. The structure of claim 22 in which said substrate is a printed circuit card in which said cured composition reinforces said solder connections.

24. The structure of claim 17 in which said assembly consists of silicon devices directly attached to a printed circuit card.

25. The structure of claim 24 in which said silicon devices are connected to the printed circuit card by flip chip attach of solder joints and said cured composition reinforces and protects said solder joints.

26. The structure of claim 24 in which said silicon devices are connected to said printed circuit card by wire bonding and said cured composition is applied as a globtop encapsulant to protect said silicon devices.

27. The structure of claim 18 in which the electronic assembly is comprised of semiconductor chips encapsulated in molded plastic which are surface mounted with said reinforced solder joints to a printed circuit card.

28. An article comprising a chemical product encapsulated by said epoxy composition defined in claim 4.

29. The article defined in claim 28 wherein said chemical product is selected from the group consisting of a pharmaceutical, a pesticide and a fertilizer.

* * * * *